(12) United States Patent
Gray

(10) Patent No.: US 6,599,612 B1
(45) Date of Patent: Jul. 29, 2003

(54) PROCESS OF FORMING A PERFORATED WEB

(75) Inventor: Brian Francis Gray, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/555,933

(22) PCT Filed: Dec. 15, 1997

(86) PCT No.: PCT/US97/23079

§ 371 (c)(1),
(2), (4) Date: Jun. 6, 2000

(87) PCT Pub. No.: WO99/30658

PCT Pub. Date: Jun. 24, 1999

(51) Int. Cl.⁷ .......................... B32B 3/24; A61F 13/517
(52) U.S. Cl. ........................ 428/132; 428/131; 428/212; 428/913; 604/378; 604/383
(58) Field of Search ................. 428/132, 131, 428/212, 913; 604/378, 383

(56) References Cited

U.S. PATENT DOCUMENTS

| | | |
|---|---|---|
| 3,707,102 A | 12/1972 | Huppenthal et al. |
| 3,942,934 A | 3/1976 | Momiyama et al. |
| 4,155,800 A | 5/1979 | Wilson |
| 4,319,868 A | 3/1982 | Riemersma et al. |
| 4,377,544 A | 3/1983 | Rasmussen |
| 4,609,518 A | 9/1986 | Curro et al. |
| 4,839,216 A * | 6/1989 | Curro et al. ................. 428/134 |
| 5,441,691 A * | 8/1995 | Dobrin et al. ............... 264/504 |
| 5,665,452 A | 9/1997 | Langdon et al. |
| 6,228,462 B1 * | 5/2001 | Lee et al. .................... 428/132 |

* cited by examiner

Primary Examiner—William P. Watkins, III
(74) Attorney, Agent, or Firm—Ingrid N. Hickman; Kevin C. Johnson

(57) ABSTRACT

A process of forming a soft and resilient web (10) exhibiting a substantially continuous pattern of debossments or apertures is disclosed. The process comprises locally heating process to melt predetermined points of the web. The process includes: continuously bringing the web (10) in contact relation with a forming structure (15) exhibiting a substantially continuous pattern of apertures (16) corresponding to the debossments or apertures of the web; locally heating the region of the web at the predetermined points along the surface of the web by an energy source (21) to give the web temperature above its melting temperature; applying a substantially uniform fluid pressure differential to the locally heated web (10) at least in those areas to be debossed or apertured, whereby the web is debossed or apertured at the predetermined points and generally maintains its surface structure at least in those areas in which the web (10) is not debossed or apertured; and removing the debossed or apertured web (10) from the forming structure (15). A soft and resilient web formed by the process is also disclosed.

6 Claims, 14 Drawing Sheets

PROCESS OF FORMING A PERFORATED WEB

FIELD OF INVENTION

The present invention relates to a process of forming a soft and resilient web and a soft and resilient web formed by the process. More particularly, the present invention relates to a process utilizing a locally heating process to form a soft and resilient web exhibiting a substantially continuous pattern of debossments or apertures. The present invention also relates to a soft and resilient web exhibiting a substantially continuous pattern of debossments or apertures.

BACKGROUND

In processes disclosed in prior art for producing a web such as a formed film, a web of heat-softened film is provided on the patterned, perforated outer surface (referred to herein as a forming surface) of a structure such as an endless belt or a drum cylindrical surface. A vacuum beneath the forming surface pulls the heat-softened film into conformity with the forming surface. Alternatively, a positive pressure may be used to force the heat-softened film against the forming surface. Whether the web of film is simply embossed or is debossed and perforated will depend on the size of the holes in the forming surface, the softness and thickness of the film being formed, and the fluid pressure differential across the film.

Processes for producing webs of embossed thermoplastic film are disclosed in U.S. Pat. No. Re 23,910 issued to Smith & Smith on Dec. 12, 1954; U.S. Pat Nos. 2,776,451 and 2,776,452 both issued to Chavannes on Jan. 8, 1957; and U.S. Pat. No. 2,905,969 issued to Gilbert & Prendergast on Sep. 29, 1959. Processes for the production of webs of debossed and perforated thermoplastic films are disclosed in U.S. Pat. No. 3,038,198 issued to Shaar on Jun. 12, 1962; U.S. Pat. No. 3,054,148 issued to Zimmerli on Sep. 18, 1962; U.S. Pat. No. 4,151,240 issued to Lucas & Van Coney on Apr. 24, 1979; U.S. Pat. No. 4,155,693 issued to Raley on May 22, 1979; U.S. Pat. No. 4,226,828 issued to Hall on Oct. 7, 1980; U.S. Pat No. 4,259,286 issued to Lewis, Sorensen & Ballard on Mar. 31, 1981; U.S. Pat No. 4,280,978 issued to Dannheim & McNaboe on Jul. 28, 1981; U.S. Pat No. 4,317,792 issued to Raley & Adams on Mar. 2, 1982; U.S. Pat. No. 4,342,314 issued to Radel & Thompson on Aug. 3, 1982; and U.S. Pat. No. 4,395,215 issued to Bishop on Jul. 26, 1983. A process for the production of perforated seamless tubular film is disclosed in U.S. Pat No. 4,303,609 issued to Hureau, Hureu & Gaillard on Dec. 1, 1981.

The processes disclosed in the references cited above require that the thermoplastic film be heat-softened in order to achieve the desired embossing or debossing and perforation of the film. This can be achieved as disclosed in many of the above references by heating an existing web of film to a temperature above its melt temperature range such that it is in a molten state and will readily flow and attain a new configuration. Alternatively, the molten film may be achieved by feeding a web of film directly from a film extruder onto the forming surface. Such a process is disclosed in U.S. Pat. No. 3,685,930 issued to Davis & Elliot on Aug. 22, 1972, where a web of thermoplastic film is extruded directly onto the outer surface of an endless belt and a vacuum is pulled beneath the belt to make the molten web of film assume the configuration of the outer belt surface. Similarly, U.S. Pat. No. 3,709,647 issued to Barnhart on Jan. 9, 1973 discloses a web of molten thermoplastic film extruded directly onto the outer cylindrical surface of a vacuum forming drum.

It is known to shape molten thermoplastic sheet material by the use of a fluid pressure forcing the sheet against a mold; such processes are disclosed in U.S. Pat. No. 2,123,552 issued to Helwig on Jul. 12, 1938; and U.S. Pat. No. 3,084,389 issued to Doyle on Apr. 9, 1963.

When webs of embossed or debossed and perforated thermoplastic film are produced on a patterned surface by the above prior art processes, it is generally necessary to cool the film below its melting temperature range to set its three-dimensional structure prior to removing the web of formed film from the forming surface. This makes the web of formed film much less susceptible to distortion of its bulk conformation.

To make webs of formed film by these prior art processes, it is necessary to have the film within or above its melting temperature range in order to form the film. This limits the range of desired properties that can be engineered into the formed film since all previous thermo-mechanical history of the film is erased.

Other attempts to produce a web, such as a formed film, are to apply a liquid pressure to the web on the forming surface. The liquid pressure has sufficient force and mass flux to cause the web to be deformed toward the forming surface such that the material acquires a substantial three-dimensional conformation. The temperature of the web of material is controlled such that it remains below the transformation temperature range of the material throughout the process. Such process is disclosed in U.S. Pat. No. 4,695,422 issued to Curro et al. on Sep. 22, 1987.

In the process disclosed in the reference, the web is exposed to the liquid pressure, however, the temperature is below the transformation temperature range of the material which does not melt the material. When the material deforms by the liquid pressure, the material substantially ruptures and the some "spring-back" of the material generally occurs after it passes the zone of liquid pressure. This "spring-back" of the material causes dimensionally unstable, three-dimensional apertures on the web which results in poor resiliency of the web.

Therefore, it is an objective of the present invention to provide a process of forming a soft and resilient web utilizing a locally heating process to form a substantially continuous pattern of debossments or apertures on the web.

It is a further objective of the present invention to provide a soft and resilient web formed by the process utilizing a locally heating process to form a substantially continuous pattern of debossments or apertures on the web.

SUMMARY

The present invention provides a process of forming a soft and resilient web exhibiting a substantially continuous pattern of debossments or apertures being formed by locally heated at predetermined points along the surface of the web. The process comprises: continuously bringing the web in contact relation with a forming structure exhibiting a substantially continuous pattern of apertures corresponding to the debossments or apertures of the web, the continuous pattern of the apertures extending from the outermost to the innermost surface of the forming structure; locally heating the region of the web at the predetermined points along the surface of the web by an energy source, the energy source heating the region of the web above its melting temperature range; applying a substantially uniform fluid pressure differential to the locally heated web at least in those regions to be debossed or apertured while the web is in contact with the forming structure, whereby the web is debossed or apertured at the predetermined points and generally maintains its surface structure at least in those areas in which the web is not debossed or apertured; and removing the debossed or apertured web from the forming structure.

The present invention also provides a soft and resilient web exhibiting a substantially continuous three-dimensional pattern of macro-apertures. The web comprises a fluid impermeable plastic material. The web has a first surface, a second surface, a multiplicity of micro-apertures and a multiplicity of macro-apertures. The web has a land area on the first surface and a wall protruding beyond the second surface of the land area. The land area includes a pattern of fine-scale, volcano-like micro-apertures comprising discrete volcano-like surface aberrations and micro-openings. The aberrations protrude from the land area beyond the first surface of the land area. The micro-opening locates at the top of each aberration. The macro-apertures are defined by the wall, an opening on the first surface surrounded by the wall and an apex opening. The wall has the micro-apertures thereon. The size of the micro-apertures on the wall is generally smaller than that of the micro-apertures on the land area.

The present invention further provides a soft and resilient web exhibiting a substantially continuous three-dimensional pattern of macro-apertures. The web comprises a fluid impermeable plastic material. The web has a first surface, a second surface, a multiplicity of micro-apertures and a multiplicity of macro-apertures. The web has a land area on the first surface and a wall protruding beyond the second surface of the land area. The land area includes a pattern of fine-scale, volcano-like micro-apertures comprising discrete volcano-like surface aberrations and micro-openings. The aberrations protrude from the land area beyond the first surface of the land area. The micro-opening locates at the top of the aberration. The macro-apertures are defined by the wall, an opening on the first surface surrounded by the wall and an apex opening. The wall has the micro-apertures thereon. The number of the micro-apertures on the wall is less than the number of the micro-apertures on the land area, per a unit area.

The present invention further provides a soft and resilient web exhibiting a substantially continuous three-dimensional pattern of apertures. The web comprises fiber aggregation. The web has a first surface, a second surface, and a multiplicity of apertures. The web has a land area on the first surface and a wall protruding beyond the second surface of the land area. The apertures are defined by the wall, an opening on the first surface surrounded by the wall and an apex opening. The land area on the first surface comprises the fiber aggregation. At least a portion of the wall comprises the fiber aggregation, and at least a portion of the fiber aggregation is melted to each other at least adjacent the apex opening of the apertures.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE INVENTION

While the present invention will be described in the context of providing three dimensional, apertured webs particularly suited for use as a wearer contacting surface on absorbent bandages such as disposable diapers, sanitary napkins, wound dressings and the like, the present invention is in no way limited to such applications. The patterns created may be of any desired shape, they may be regulated or random, reticulated or non-reticulated, continuous or interrupted, or any desired combination thereof. The detailed description of the structures disclosed herein and their suggested use as topsheets and/or backsheets in a disposable absorbent bandage context will allow one skilled in the art to readily adapt the invention to produce webs well suited to other applications.

Figure 1:
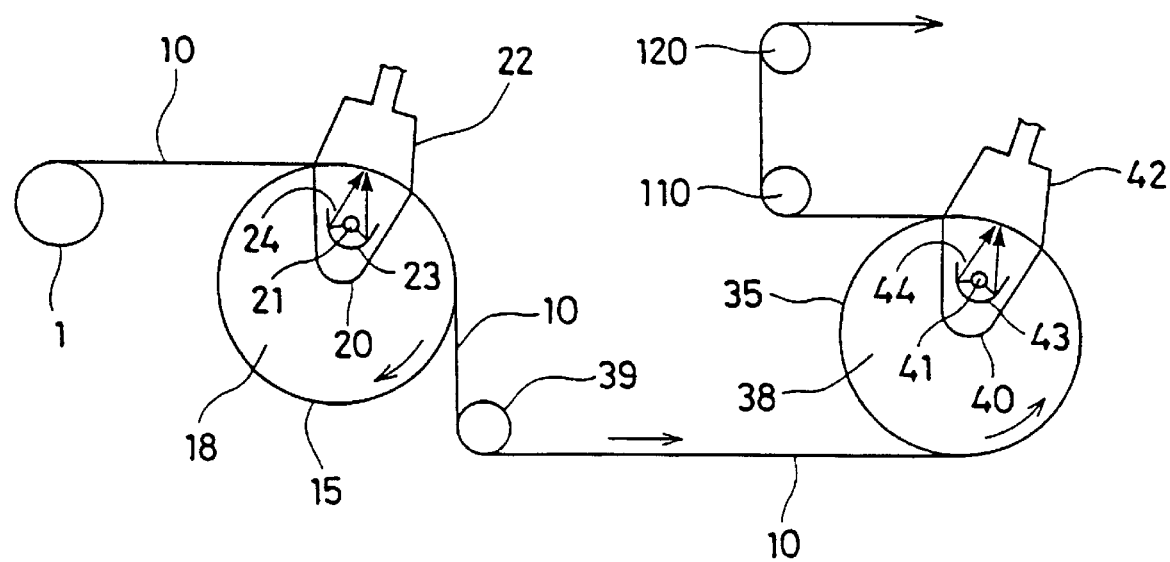
FIG. 1 is a simplified schematic view of a web forming process of the present invention including two phase process.

A particularly preferred multi-phase, continuous forming process of the present invention is schematically illustrated in FIG. 1. In the embodiment shown in FIG. 1, a substantially planar web 10 which may be comprised of, e.g., a thermoplastic film, a fiber aggregation, or a combination of a fiber aggregation and a thermoplastic film is fed from a supply roll 1 onto the surface of a first forming drum 18 about which a forming structure 15 continuously rotates at substantially the same speed as the incoming web. The forming drum 18 preferably includes an internally located vacuum chamber 20 and an energy source 21 such as a radiant energy source which is preferably stationary relative to the moving forming structure 15. The forming drum 18 may further include a reflector 23. An air jet means 22 is also provided adjacent the outside surface of the forming structure 15 opposite the vacuum chamber 20.

Figure 2:
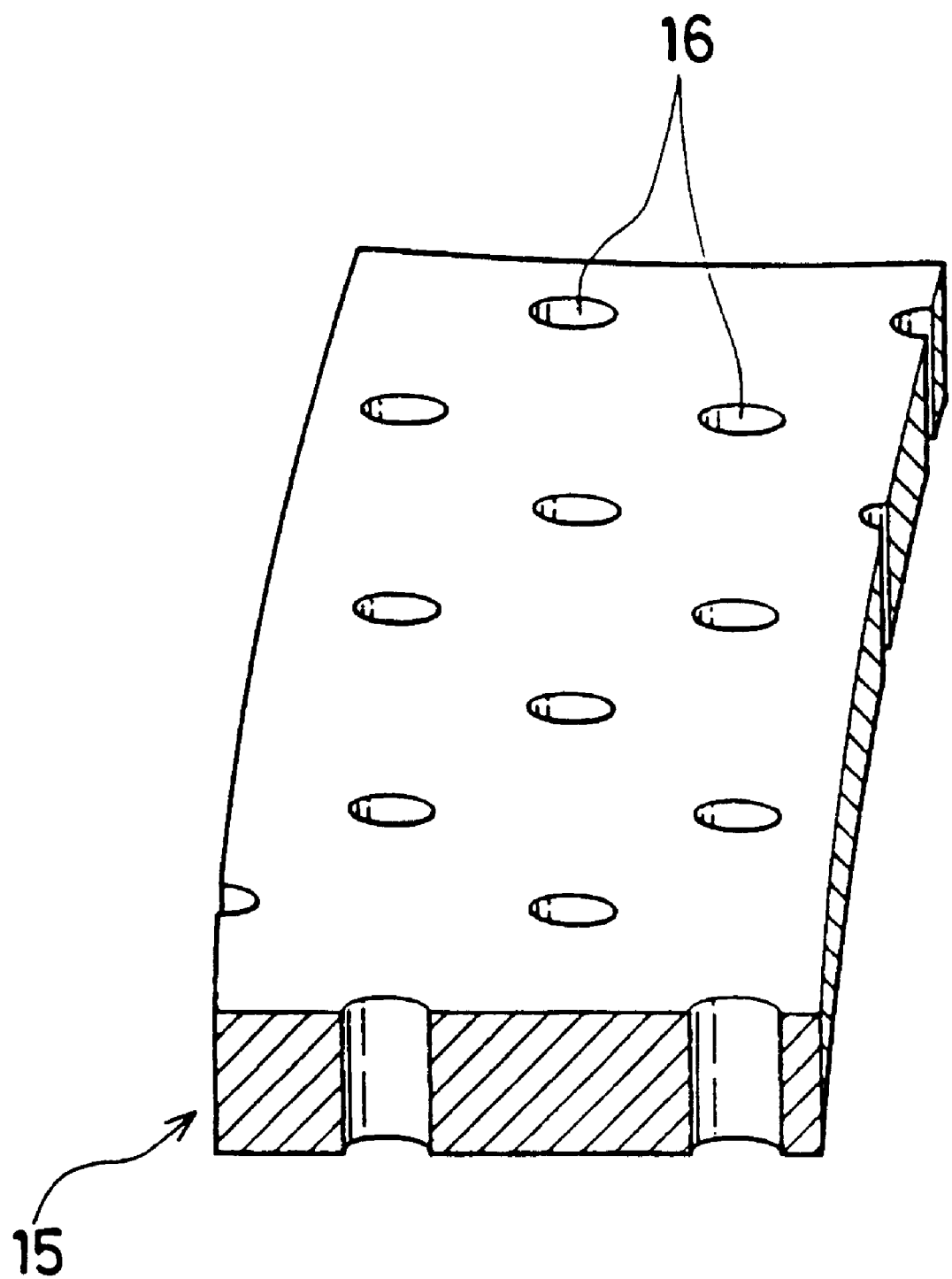
FIG. 2 is an enlarged fragmentary perspective view of the first forming structure utilized to support the web when the web is subjected to a first phase shown in FIG. 1.

Forming structure 15, a greatly enlarged fragmentary segment of which is illustrated in FIG. 2, includes a multiplicity of relatively small apertures 16 across all or any desired portion of its surface. For disposable absorbent article topsheet applications these apertures typically range in size between about 0.05 mm and about 0.5 mm in diameter. Their spacing may be in a regular pattern or it may vary randomly, as desired, in the resultant plastic film 10. Methods for constructing suitable three-dimensional tubular forming members of this general type are disclosed in commonly assigned U.S. Pat. No. 4,503,256 issued to Radel et al. On Apr. 2, 1985 and commonly assigned U.S. Pat. No. 4,509,908 issued to Mullane, Jr. on Apr. 9, 1985, said patents being hereby incorporate herein by reference.

The apertures 16 in the forming structure 15 may be of any desired shape or cross-section when the forming structure is fabricated utilizing the laminar construction techniques generally disclosed in the aforementioned commonly assigned patents. Alternatively, the tubular shaped forming structure 15 may be comprised of non-laminar construction and the desired pattern of apertures 16 created by means of laser drilling or the like. It is also possible to use belts or the like comprised of pliable material and operating continuously about a pair of rolls. In the latter circumstance, it is generally desirable to provide suitable support beneath the pliable belt while it is subjected to the fluid pressure differential in order to avoid distortion.

Figure 3:
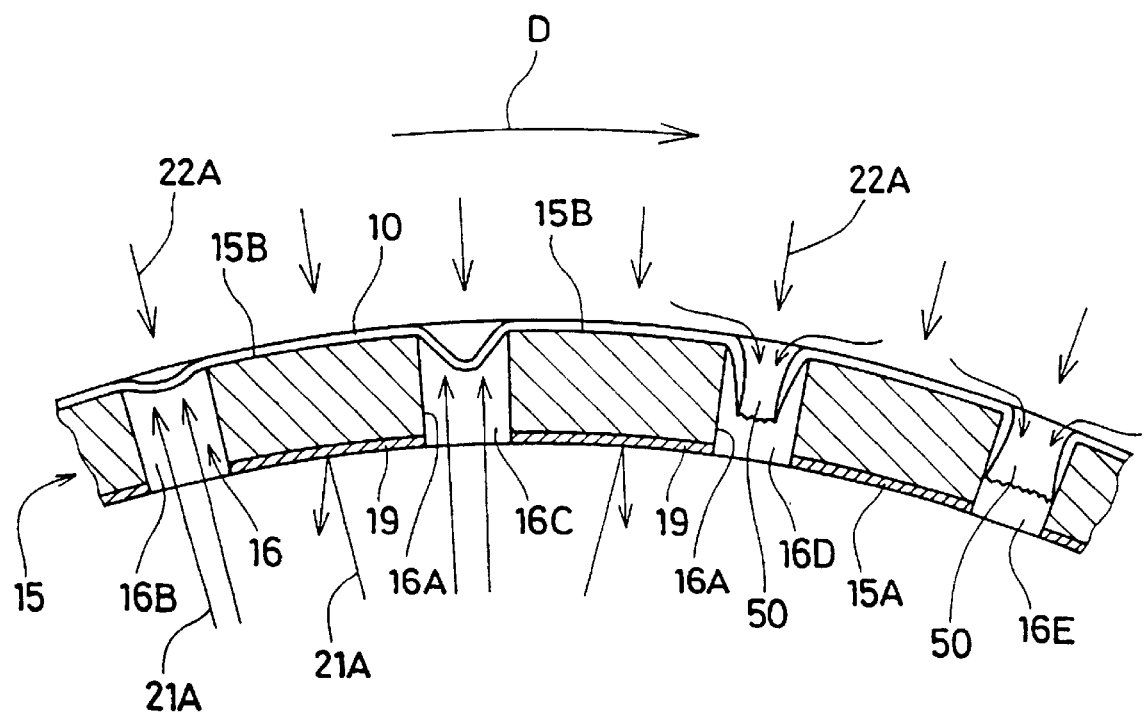
FIG. 3 is an enlarged cross-sectional view of the web which is supported on the surface of the first forming structure of the first phase shown in FIG. 1 when the web is subjected to a fluid pressure differential and a locally heating energy.

It is preferable that the physical characteristics of the incoming web be substantially maintained in the regions of the web that overlay the area of the forming structure that are not aligned with the apertures 16. This is, at least in part achieved by ensuring that the outer surface of the forming structure 15 is not heated to the temperature above the melting temperature of the incoming web. This may be achieved by coating the inside surface 15A of the forming structure 15 with a reflective material 19 to reflect the radiant energy 21A generated by the energy source 21 as shown in FIG. 3. The aperture walls 16A may also be coated with this reflective material. The reflective material 19 may, for example be nickel plating or any other coating that effectively adheres to the inside surface 15A while substantially reflecting the type of energy being used as a source. Alternately, the inside surface 15A and/or the wall 16A may be laminated using a reflective material. It is preferable to select appropriate reflective coatings based on their absorbency to the frequency spectrum of the energy source. To minimize conductive heat transfer from the inside surface 15A to the outside surface 15B, layers of the forming structure 15 can be constructed of low thermal conductivity materials such as ceramics or high service temperature plastics. A semi-continuous layer internal to the forming structure 15 may be used to create interior voids further reducing thermal conduction to the outer surface 15B. Other approaches to reduce conductive heat transfer to the web may include texturing of the outer surface of the forming structure 15B to minimize physical contact with the web. Additionally, the forming structure 15 may be precooled as it rotates in order to further reduce the peak temperature that the outer surface 15B reaches during the forming process. This may take the form of an air jet of cool air incident on the forming structure 15 immediately upstream of the location where the plastic film 10 is introduced. Alternatively, an additional vacuum plenum may be added internally to the forming structure 15 in a similar location to the above example to draw air through the forming structure thus cooling it prior to introduction of the plastic film 10.

The energy source 21 generates the radiant energy 21A and the radiant energy source 21A melts at least a part of the plastic web 10. The radiant energy 21A reaches the part of the plastic film 10 which is supported on the surface of the forming structure 15 through the apertures 16 of the forming structure 15. The radiant energy 21A heats a part of the plastic film 10 to a temperature above its melting temperature range such that a part of the plastic film 10 is in a molten and/or flowable state. The energy source 21 may take the form of a substantially targeted flux of electromagnetic radiation such as that provided by an infra-red radiant heater. This type of heater may be used to direct an electromagnetic energy flux towards a targeted area on the inside surface 15A of the forming structure 15. Radiant thermal heaters of this type are commercially available, emitting infra-red radiation at a predetermined and preferred wavelength. Further, these heaters can be equipped with variously shaped parabolic reflectors. The parabolic reflector serves to provide a concentrated parallel flux of radiant energy in a confined beam or, alternately, can target the energy flux at a predetermined focal point thus further intensifying the energy flux over this region. The energy flux incident on the plastic film 10 at the points co-incident with the apertures 16 must be sufficient to melt the plastic film 10 such that it can be induced to substantially conform to the apertures 16 by the fluid pressure differential. Although the above is one preferred embodiment of the energy source, the source can take many alternate forms. These may include lasers or other frequencies of electromagnetic radiation.

It is desired that the temperature of the outside surface 15B be maintained below the melting temperature of the plastic film 10 so as to maintain the physical structure of the incoming web in the areas not located above the apertures 16. It is therefore preferable that the energy flux be targeted on a limited arc or region of the inside surface 15A. This minimizes the opportunity for substantial thermal conduction to the outside surface 15B, which would result in an undesirable increase in temperature for this surface. The energy flux should be of sufficient intensity so as to melt the plastic film 10 through the apertures 16 while permitting the duration of the energy incident on the inside surface 15A to be minimized. It is known that the absorption co-efficient of polymers varies as a function of the frequency of the incident electromagnetic energy source. Therefore, the frequency of the energy source should typically be selected to maximize the energy absorbed by the plastic film 10. At the same time, the reflective coating 15A on the inner surface of the forming structure 15, should be selected such that the maximum amount of energy incident on this surface 15A is reflected. Appropriate selection and balancing of these two design parameters contributes to a robust process.

A reflector 23 directs a part of the radiant energy 21A towards a desired region on the inner surface 15A of the forming structure 15. The reflector 23 preferably has a parabolic shape with an opening 24 which faces the inside surface 15A of the forming structure 15 and extends along the length of the energy source 21. The reflector 23 may focus the radiant energy 21A onto a very narrow region on the inner surface 15A of the forming structure 15 in a circumferential direction. It may focus the radiant energy 21A into a predetermined area on the inner surface 15A of the forming structure 15. The reflector 23 may have any preferred cross-sectional profile, such as a parabola. The reflector 23 is preferably made of metal coated with a highly emissive material such as nickel so as to reflect the radiant energy 21A very effectively. The reflector 23 may for example, be made by electroplating a pre-formed thin metal plate. Such reflectors are commercially available from suppliers such as OGDEN Mfg. Co. (USA) and are often an integral component of a radiant heater.

A differential pressure is applied across the plastic film 10 between the air jet means 22 and inner chamber 20 and in the region along the circumference of the forming structure 15 where the plastic film 10 is locally melted. The air jet means 22 approximately coincides with the beginning and the end of the inner chamber 20 and is located adjacent the outside surface 15B of the forming structure 15. In this region, a substantially uniform fluid pressure differential is applied to the plastic film 10. This may be applied by means of a positive pressure (high pressure) within the air jet means 22, a partial vacuum (low pressure) within the chamber 20 or a combination of these two conditions. Thus, a substantial differential pressure is applied to the substantially planar web of the polymeric web 10 as it passes across the suction chamber. The high pressure air 22A which is generated by the air jet means 22 may be preheated to a temperature below the softening temperature of the plastic film 10 to help to make more dimensionally stable micro-apertures 50. Alternatively, the high pressure air 22A may be precooled to help further maintain the thermo-mechanical history given to the plastic film 10 which is not located on the apertures 16 of the forming structure 15. The high pressure air 22A may be precooled to a temperature below the plastic film temperature before the plastic film 10 is provided on the forming structure 15.

As shown in FIG. 3, the forming structure 15 rotates in the direction D with the plastic film 10. FIG. 3 shows four sequential apertures 16B, 16C, 16D and 16E of the forming structure 15 as it rotates in the downstream direction D. At the aperture 16B at the upstream end, the energy source 21 gives the radiant energy 21A to the plastic film 10 from the inside of the forming structure 15 through the aperture 16B to soften the plastic film 10. Since there is an inward pressure differential 22A applied in this region, the softened plastic film 10 is deformed slightly inward. While the forming structure 15 rotates toward the position of the aperture 16C shown in FIG. 3, the plastic film 10 receives more radiant energy 21A and the softened plastic film 10 deforms further into the aperture 16. As the forming structure 15 further rotates, the softened plastic film 10 locally melts, rupturing and debossing as shown at the position of the aperture 16D making the aperture 50 in the plastic film 10. While the forming structure 15 continues to rotate from the position of the aperture 16D to 16E, the plastic film 10 receives more radiant energy 21A and high air pressure 22A flowing through the newly formed film aperture 50. This causes the plastic film 10 to further conform to the shape of the aperture 16 of the forming structure 15 and the aperture 50 to become more stable to form a fine-scale, three-dimensional, volcano-like micro-aperture 50. During the process, regions of the polymeric film 10 not located above the apertures 16 of the forming structure 15 are not heated beyond the melting temperature range of the resin. Therefore, the thermo-mechanical history previously existing in the film is maintained in these regions.

Figure 4:
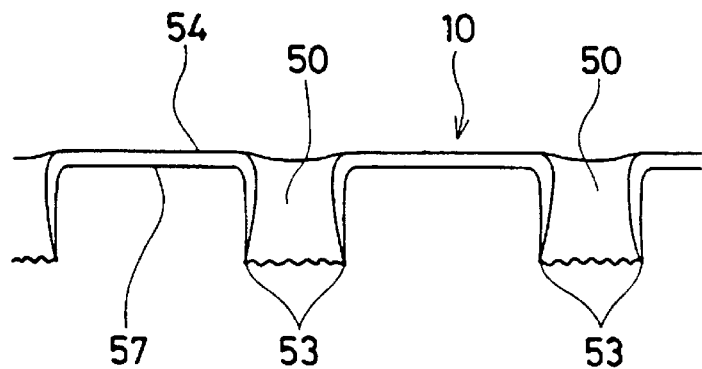
FIG. 4 is an enlarged inset of the web after it has been removed from the first forming structure of the first phase shown in FIG. 1.

After the plastic film 10 is apertured, the finely apertured plastic film 10 is removed from the surface of the first fine-scale forming structure 15 about an idler roll 39 in the condition illustrated in greatly enlarged form in the inset of FIG. 4. Because the plastic film 10 is molten only at a portion over the apertures 16 of the forming structure 15 during the forming process, it can be more easily removed from the forming structure 15 requiring only a shorter time period for cooling the plastic film 10. This has the further advantage of permitting increased processing speeds and web stability and/or a broader range of plastic webs that would otherwise lack stability in alternate processes. This further increases the flexibility to obtain finished webs of greater wearer acceptance by using, for example, incoming webs of lower basis weight or lower density resins to increase flexibility and thus softness of the micro-apertures.

Because of the presence of the fine-scale, three-dimensional, volcano-like micro-apertures 50 and fine cusps 53, the first surface 57 which contacted forming structure 15 exhibits a much softer tactile impression than the second surface 54 which was contacted by the high pressure air 22A. Accordingly, the first surface 57 of the plastic film 10 is generally preferred as the wearer contacting surface over the second surface 54.

As will be appreciated by those skilled in the art, the degree of conformance of the plastic web 10 to the surface of the forming structure 15 and the size of the apertures created therein will be influenced by factors such as the temperature of the film 10 at the time it is subjected to the high pressure air 22A, the pressure at which the air jet means 22 is applied to the surface of the film, the temperature of the air, the mass flux of the air, etc. More importantly, the degree of conformance and the size of the apertures may be influenced by the type of radiant energy, intensity of radiant energy, flux of radiant energy, etc. In general, when the fluid pressure differential is applied to the web, the lower the viscosity of the plastic film 10 being locally heated, the greater will be the degree of conformance and aperturing. In addition, the less the temperature of the plastic film 10 in the regions not located above the apertures 16 is altered from its original state, the less the thermo-mechanical history is altered.

After completion of the first phase of the web forming process disclosed in FIG. 1, the finely apertured plastic film 10 may be fed to the second phase of the forming process for macroscopic expansion or to a rewind station for temporary storage. In the latter circumstance, application of the second phase of the process may be deferred until a later date, perhaps at a different location. Alternatively, the finely apertured plastic film 10 may be utilized without further processing in an end product wherein fluid permeability and a soft tactile impression are particularly desirable, but a macroscopically expanded, three-dimensional cross-section is not essential.

Because of the desirable tactile impression imparted to the first surface 57 of the plastic film 10 in the embodiment illustrated in FIG. 1, the plastic film 10 which is to undergo macroscopic, three-dimensional expansion is preferably fed onto a second forming structure 35 which operates about forming drum 38 so that its opposite second surface 54 is placed in contact with the second forming structure 35. The forming drum 38, which may be generally similar to the forming drum 18 includes a stationary vacuum chamber 40 located adjacent the interior of the forming structure 35 and an energy source 41, both of which may be generally similar structure to the chamber 20 and the energy source 21 respectively. The forming drum 38 may further include a reflector 43, which also may be generally similar to the reflector 23. An air jet means 42 is also provided adjacent the outside surface of the forming structure 35 opposite the vacuum chamber 40. Because the macroscopic cross-section of forming structure 35 is considerably different than that of forming structure 15, the pressure and mass flux rates of the air jet means 42 are preferably adjusted independently of the pressure and mass flux rates used for the air jet means 22. The radiant energy generated by the energy source 41 is also preferably adjusted independently of the radiant energy of the radiant energy source 21.

Figure 5:
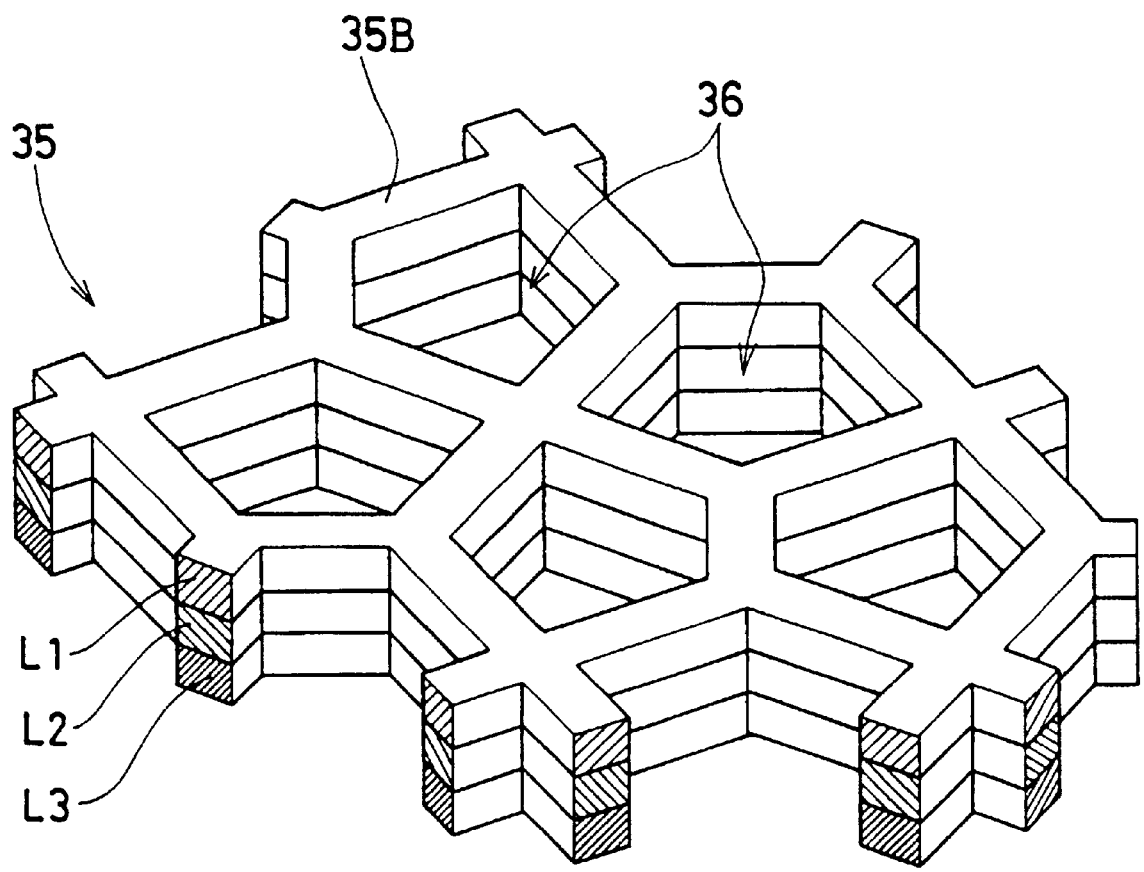
FIG. 5 is an enlarged fragmentary perspective view of the second forming structure utilized to support the web when the web is subjected to a second phase shown in FIG. 1.
Figure 6:
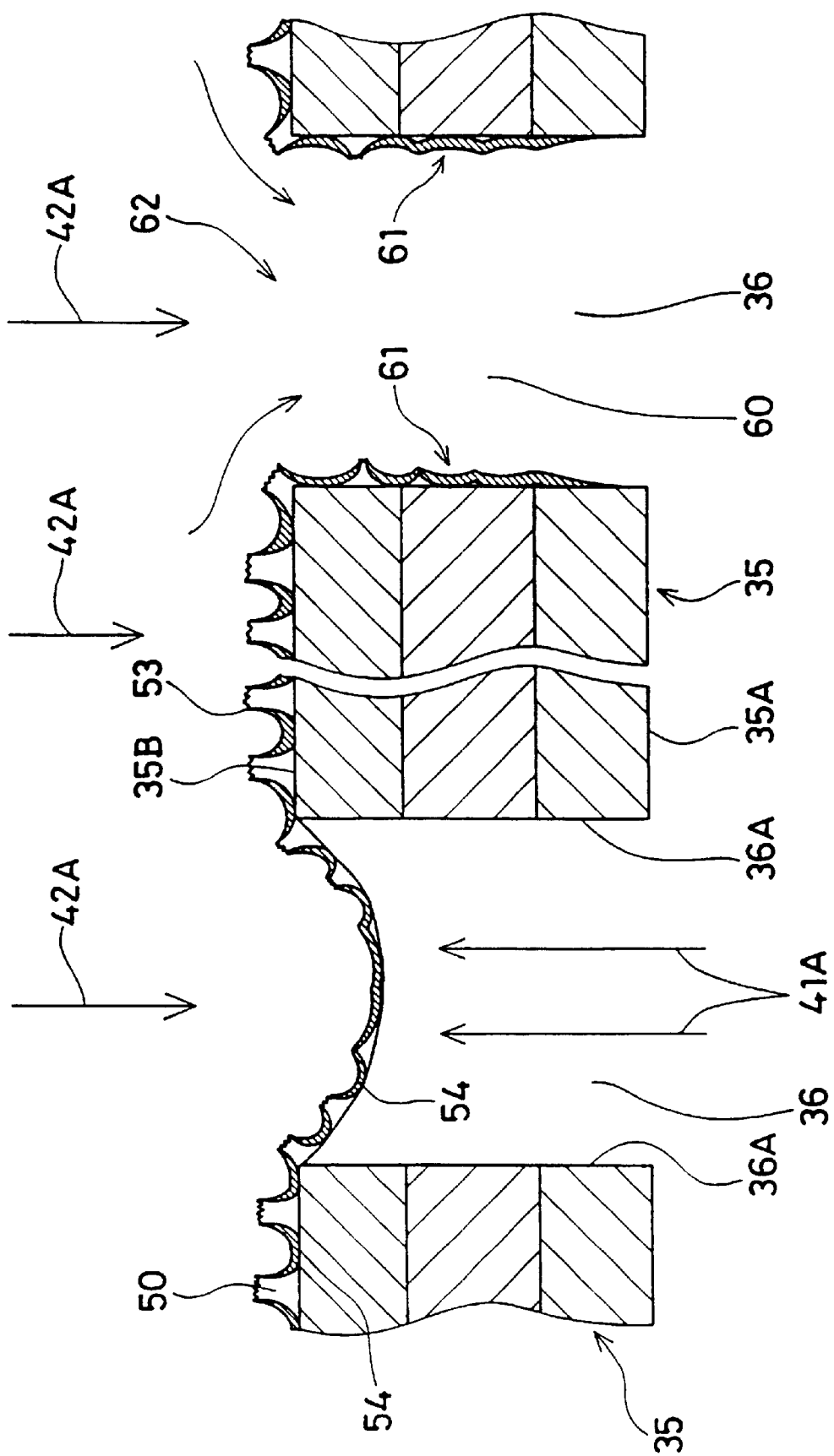
FIG. 6 is an enlarged cross-sectional view of the web which is supported on the surface of the second forming structure of the second phase shown in FIG. 1 when the web is subjected to a fluid pressure differential and a locally heating energy.
Figure 7:
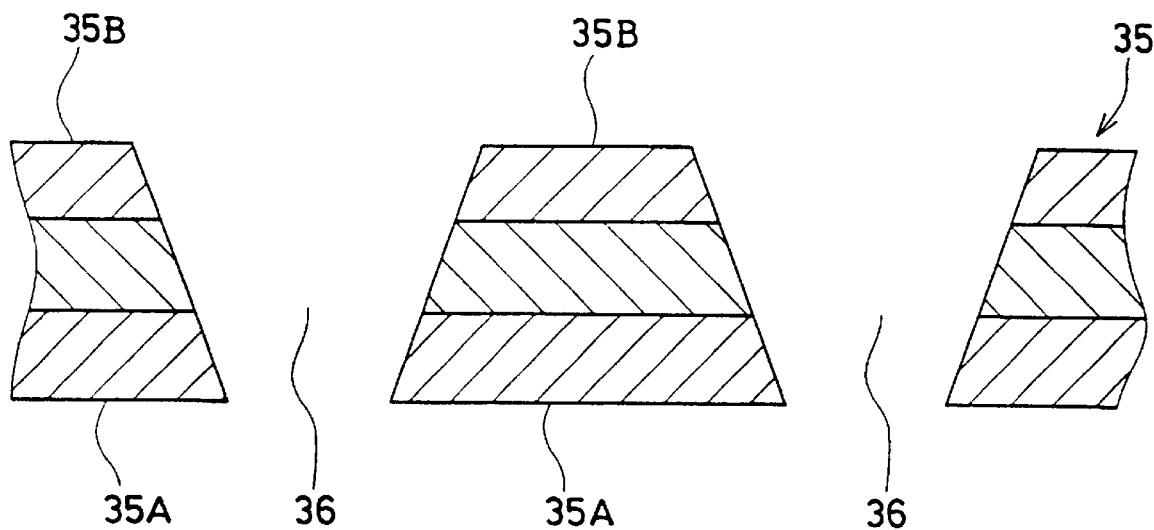
FIG. 7 is an enlarged cross-sectional view of the alternative embodiment of the forming structure.
Figure 8:
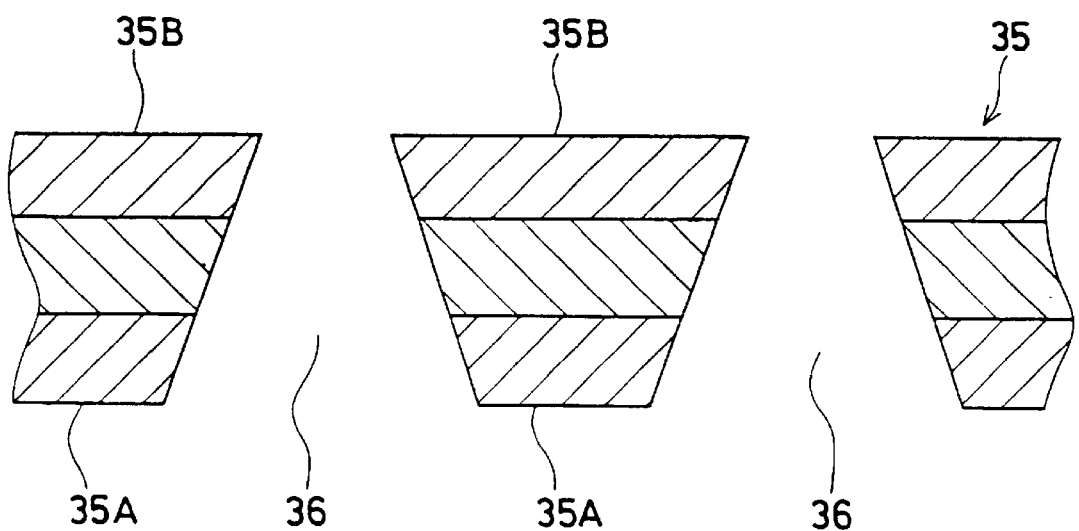
FIG. 8 is an enlarged cross-sectional view of the alternative embodiment of the forming structure.

The macroscopic cross-section of forming structure 35 is visible in the greatly enlarged fragmentary perspective of FIG. 5. The forming structure 35 exhibits a substantially continuous three-dimensional pattern including a multiplicity of apertures 36. Although not limited to these dimensions, for disposable absorbent article topsheet applications, these macro-apertures typically range in size from 0.3 to 3.0 mm and are typically at least 4 times as big as the fine-scale small apertures 16 of the forming structure 15. The forming structure 35 has the outside surface 35B and the inside surface 35A. The forming structure 35 may comprise a plurality of layers. In the embodiment shown in FIG. 5, the forming structure 35 includes three layers L1, L2 and L3. Each of the layers may have a different thermal conductivity from layer to layer in order to minimize heat transfer to the plastic film 10 supported on the outer surfaces 35B. This is so that the outer surface of the forming structure 35B is not heated above the melting temperature range of the plastic film 10. Alternatively, the inside surface 35A of the forming structure 35 may be coated with a reflective material in order to reflect the radiant energy generated by the energy source 41. The wall of the apertures 36A also may be coated by the reflective material or laminated with the reflective material. As shown in FIG. 6, the wall of the apertures 36A may be generally at a right angle to the outside surface 35B and the inside surface 35A. Alternatively, the wall 36A of the apertures 36 may be angled relative to the inner surface such that the size of the apertures 36 becomes smaller from the outside surface 35B towards the inside surface 35A as shown in FIG. 7. Alternatively, the wall 36A of the apertures 36 may be angled relative to the inner surface such that the size of the apertures 36 becomes larger from the outside surface 35B towards the inside surface 35A as shown in FIG. 8.

As is more readily apparent from the inset of FIG. 6, the plastic film 10 containing the fine-scale, volcano-like micro-apertures 50 is fed onto the outside surface 35B of the forming structure 35 such that its second surface 54 contacts the forming structure 35, while its first surface 57 is oriented toward the air jet means 42. Accordingly, the small cusps 53 of the micro-apertures 50 are oriented toward the air jet means 42.

The regions of the plastic film 10 with the fine-scale, volcano-like micro-apertures 50, which are located above the apertures 36 of the forming structure 35, receive the radiant energy 41A generated by the energy source 41. Thereby, the regions of the plastic film 10 receiving the radiant energy 41A are locally heated above the film softening temperature. The region of the plastic film 10 locally heated is also exposed to high pressure air 42A and deforms toward the inside of the forming structure 35. As the forming structure 35 rotates, the region of the plastic film 10 receives more radiant energy 41A and high pressure air 42A. The region of the plastic film 10 further deforms into the aperture 36 and finally ruptures to form the macro-apertures 60 surrounded by a wall 61 on the plastic film 10. As the forming structure 35 rotates further, the region of the plastic film 10 further melts, and the plastic film 10 substantially conforms to the shape of the apertures 36. Since the plastic film 10 is melted and conforms to the shape of the apertures 36, the shape of the macro-apertures 60 corresponding to the apertures 36 become substantially regular and thus the plastic film 10 with the dimensionally stable macro-apertures 60 becomes substantially dimensionally stable and resilient. During this process, because a region of the wall 61 of the plastic film 10 melts, the fine scale, volcano-like micro-apertures 50 on the wall 61 tend to disappear such that the wall 61 of the plastic film 10 conforms to the apertures 36 of the forming structure 35 and is substantially without micro-apertures. On the other hand, the region of the plastic film 10 which contacts the outside surface 35B of the forming structure 35 does not receive the radiant energy 41A, the forming structure 35 also being constructed so as to minimize heat transfer to these portions of the plastic film 10. The high pressure air 42A also does not change the surface structure of the plastic film 10. Therefore, the fine-scale volcano-like micro-apertures 50 which are oriented toward the air jet means 42 do not disappear and remain on the surface of the plastic film 10.

After completion of the second phase the macroscopically expanded, three-dimensional, apertured plastic web 10 is removed from the forming structure 35 and wrapped about idler rolls 110 and 120 from where it may be fed either to a rewinding station for temporary storage or directly to converting lines where it may be applied to making finished product structures, such as disposable absorbent articles.

In the above multi-phase forming process, the first phase may comprise any conventional process which forms apertures on incoming web, such as a process using a liquid pressure differential across the web or a process using an air pressure differential across the web while the entire web is in the molten state. The first phase may be directly coupled to the second phase to form an integral multi-phase process, or may be conducted separately and a roll of material unwound into the second phase described above for final forming.

Figure 9:
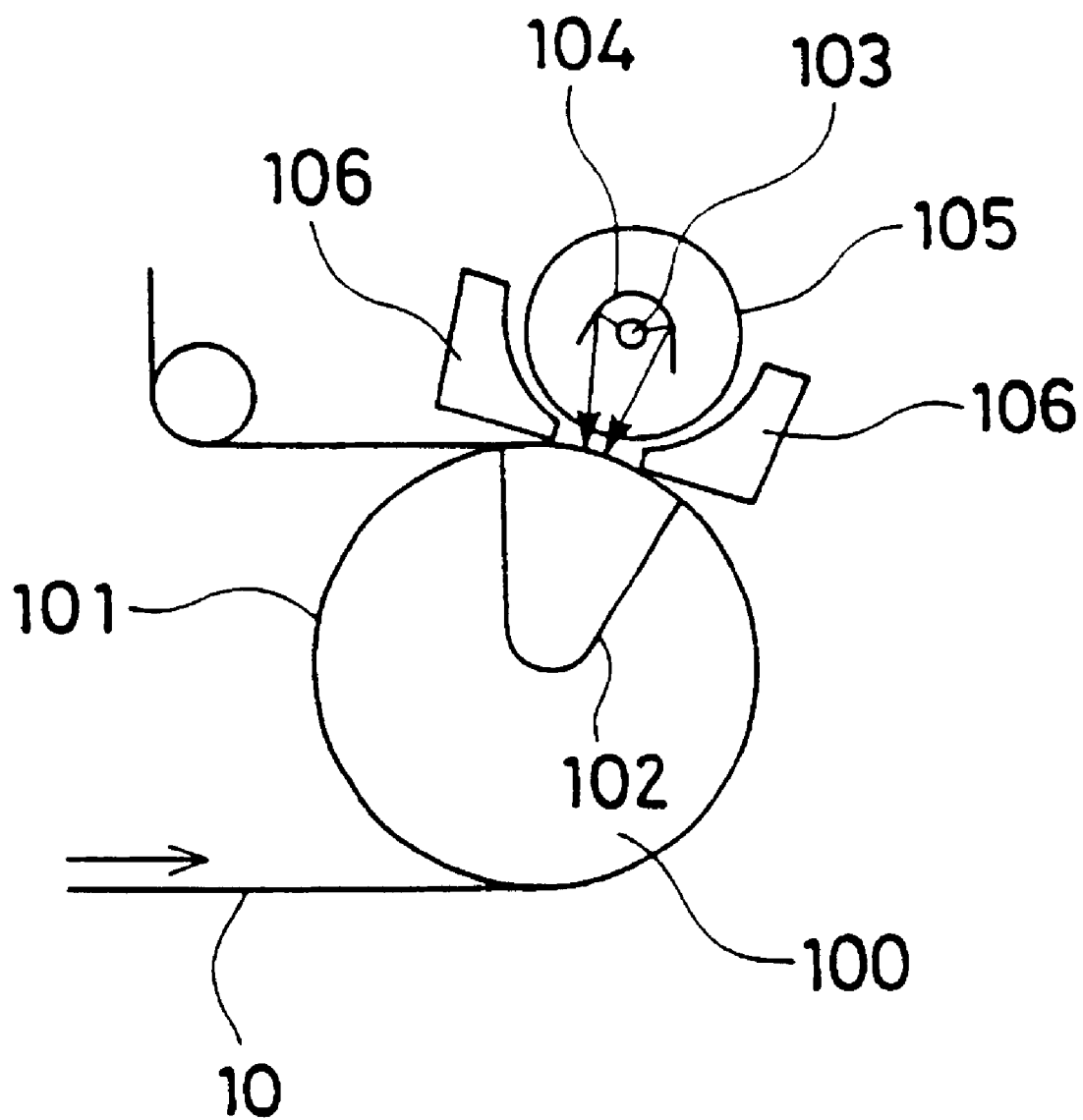
FIG. 9 is a simplified schematic view of the alternative embodiment which may be utilized for a part of the two phase process shown in FIG. 1.
Figure 10:
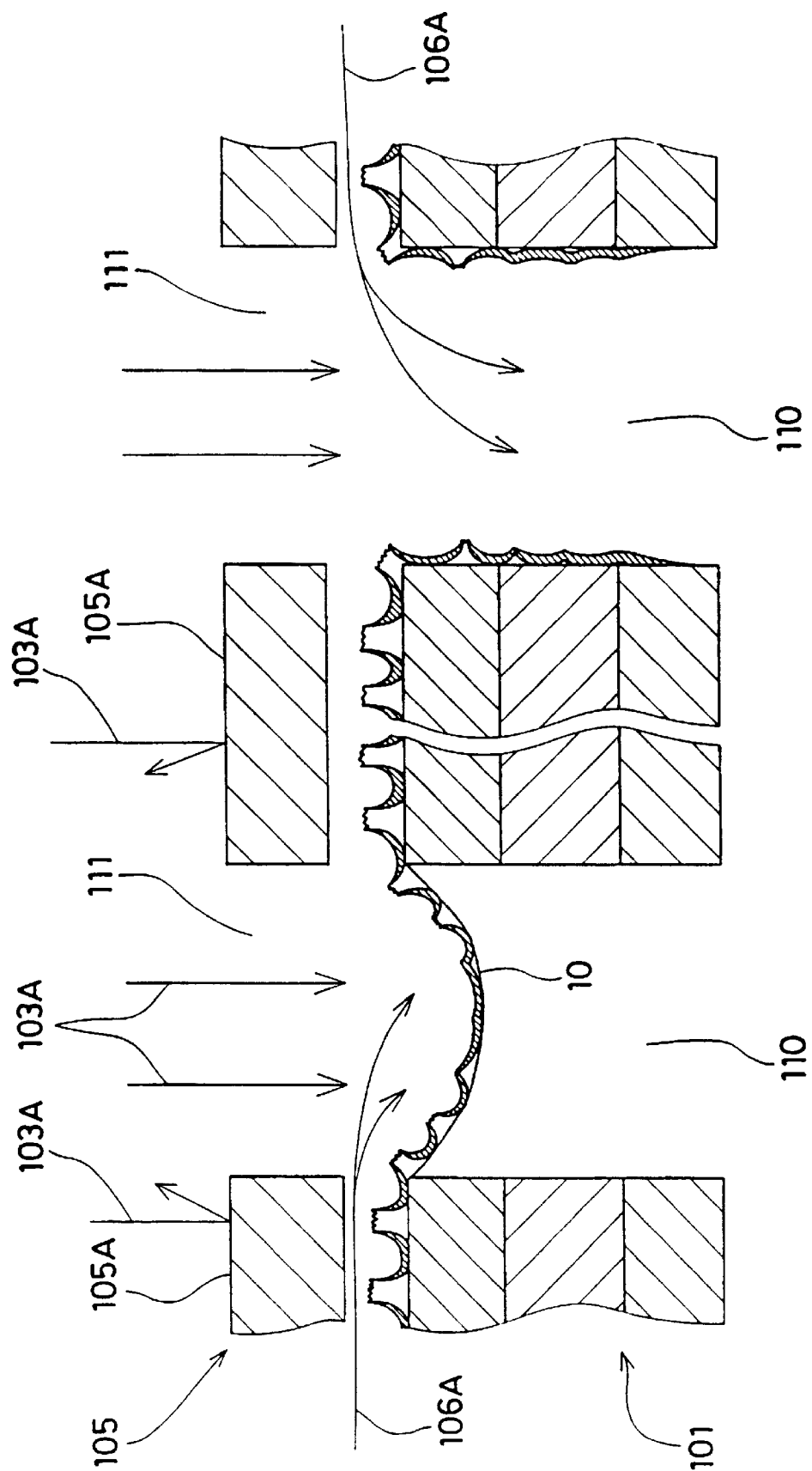
FIG. 10 is an enlarged cross-sectional view of the web which is supported on the surface of the forming structure of the alternative embodiment shown in FIG. 9 when the web is subjected to a fluid pressure differential and a locally heating energy.

FIGS. 9 and 10 show alternative embodiment of a forming process of the present invention which may be used for either or both of the first or second phases in the above two-phase forming process. The alternative shown in FIGS. 9 and 10 is suitable especially for the second process. In the embodiment shown in FIG. 9, the plastic film 10 may be fed onto the surface of a forming drum 100 about which a forming structure 101 continuously rotates at substantially the same speed as the incoming web 10. The forming drum 100, which may be generally similar to the forming drum 38, may include a stationary vacuum chamber 102, which may be generally similar structure to the chamber 40, located adjacent the interior of the forming structure 101. An energy source 103 with a reflector 104 may be disposed outside the forming structure 101. The energy source 103 may be covered by a shield screen 105 with a pattern of apertures and air jet means 106 may be provided adjacent the outside surface of the forming structure 101.

The forming structure 101 has a pattern of apertures 110 which may be generally similar to the pattern of the apertures 36 on the forming structure 35. The shield screen 105 which has a cylindrical shape rotates at substantially the same speed as the forming structure 101. The shield screen 105 may have a pattern of apertures 111 on the surface generally identical to the pattern of the apertures 110 on the forming structure 101. As the shield screen 105 rotates with the forming structure 101, each of the apertures 111 on the shield screen 105 and each of the apertures 110 on the forming structure 101 correspond to each other as shown in FIG. 10. The shield screen 105 comprises a material which reflects at least a part of the radiant energy 103A generated by the energy source 103. Alternatively, at least the inside 105A of the shield screen 105 may be coated by the reflective material or laminated with the reflective material. The energy source 103 provides radiant energy 103A to the region of the plastic film 10 through the aperture 111 from the inside of the shield screen 105 such that the region of the plastic film 10 is locally heated. As the region of the plastic film 10 receives more radiant energy 103A, the region of the plastic film 10 softens and melts. The air jet means 106 applies high pressure air 106A to the plastic film 10 and/or the vacuum chamber 102 draws air to pull the softened region of the plastic film 10. Thereby, a fluid pressure differential is provided across the plastic film 10 by a pressure gradient from the air jet means 106 toward the vacuum chamber 102. While the energy source 103 locally heats and melts the region of the plastic film 10 which corresponds to the apertures 111 of the shield screen 105, the shield screen 105 prevents the region of the plastic film 10, which is shielded from the radiant energy 103A, from being substantially heated, thereby retaining its original form. After completion of the process, the plastic web 10 is removed from the forming structure 101 and may be forwarded down stream. The high pressure air 106 may be pre-heated or pre-cooled in order to further stabilize the process as previously described.

Figure 11:
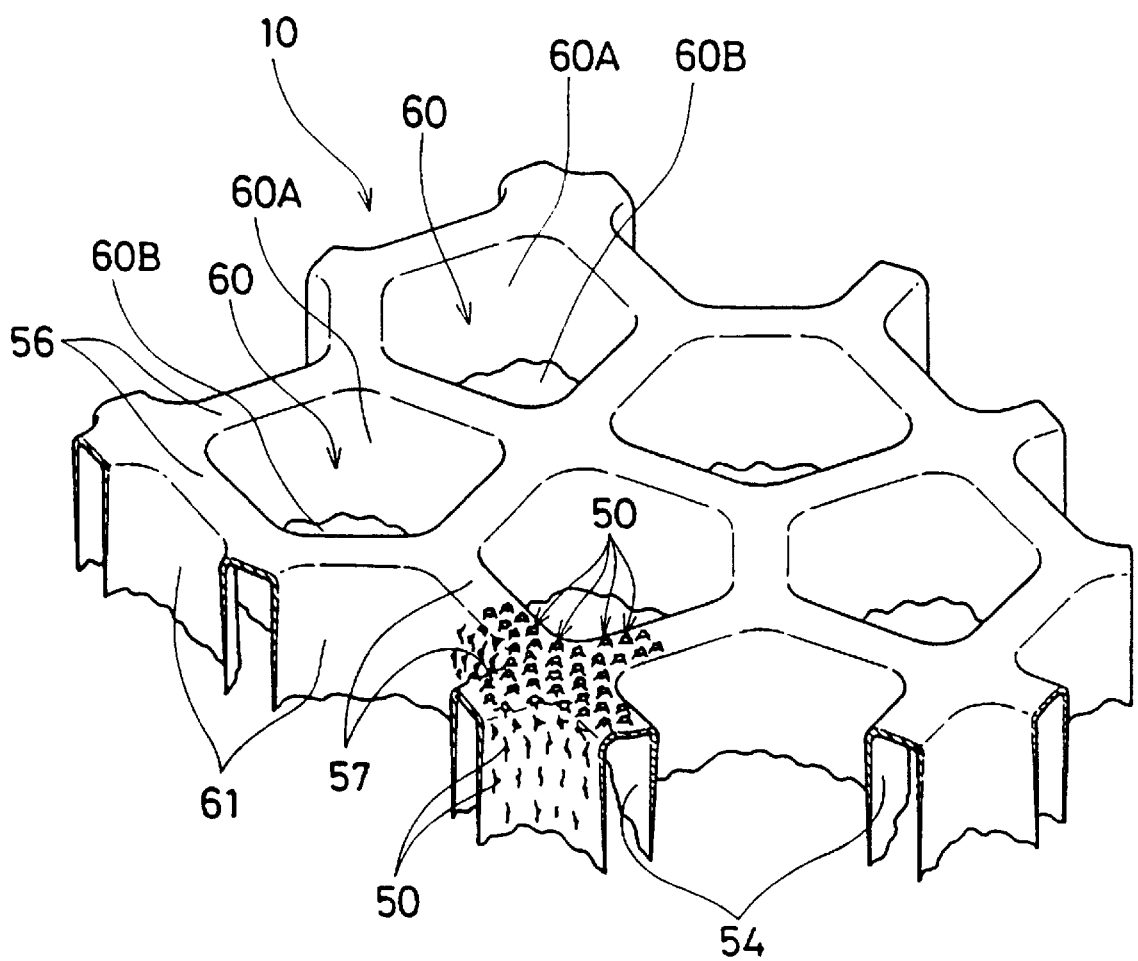
FIG. 11 is an enlarged fragmentary perspective view of a plastic film after completion of the web forming process.
Figure 12:
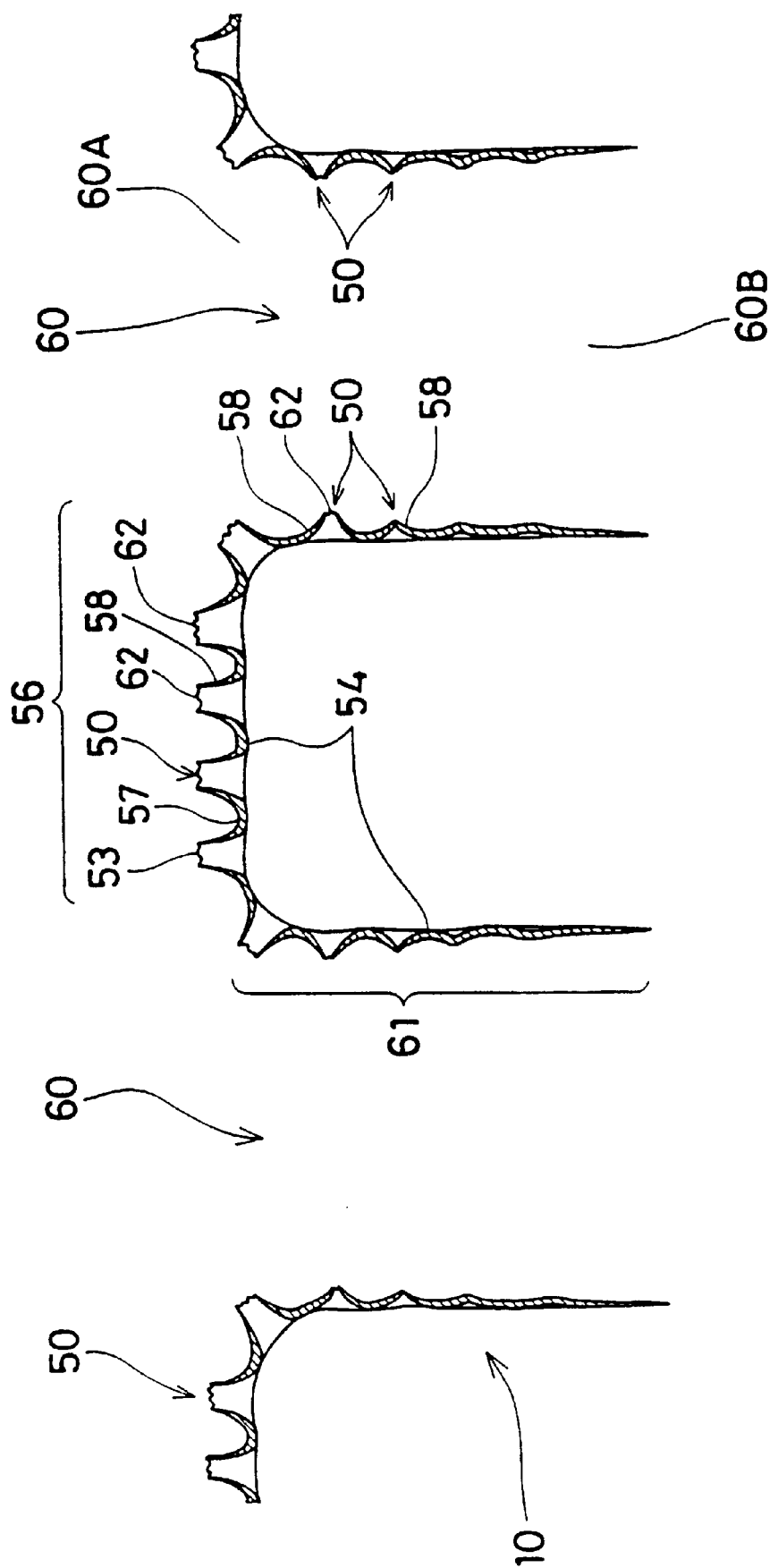
FIG. 12 is an enlarged cross-sectional view of the plastic film after completion of the web forming process.
Figure 13:
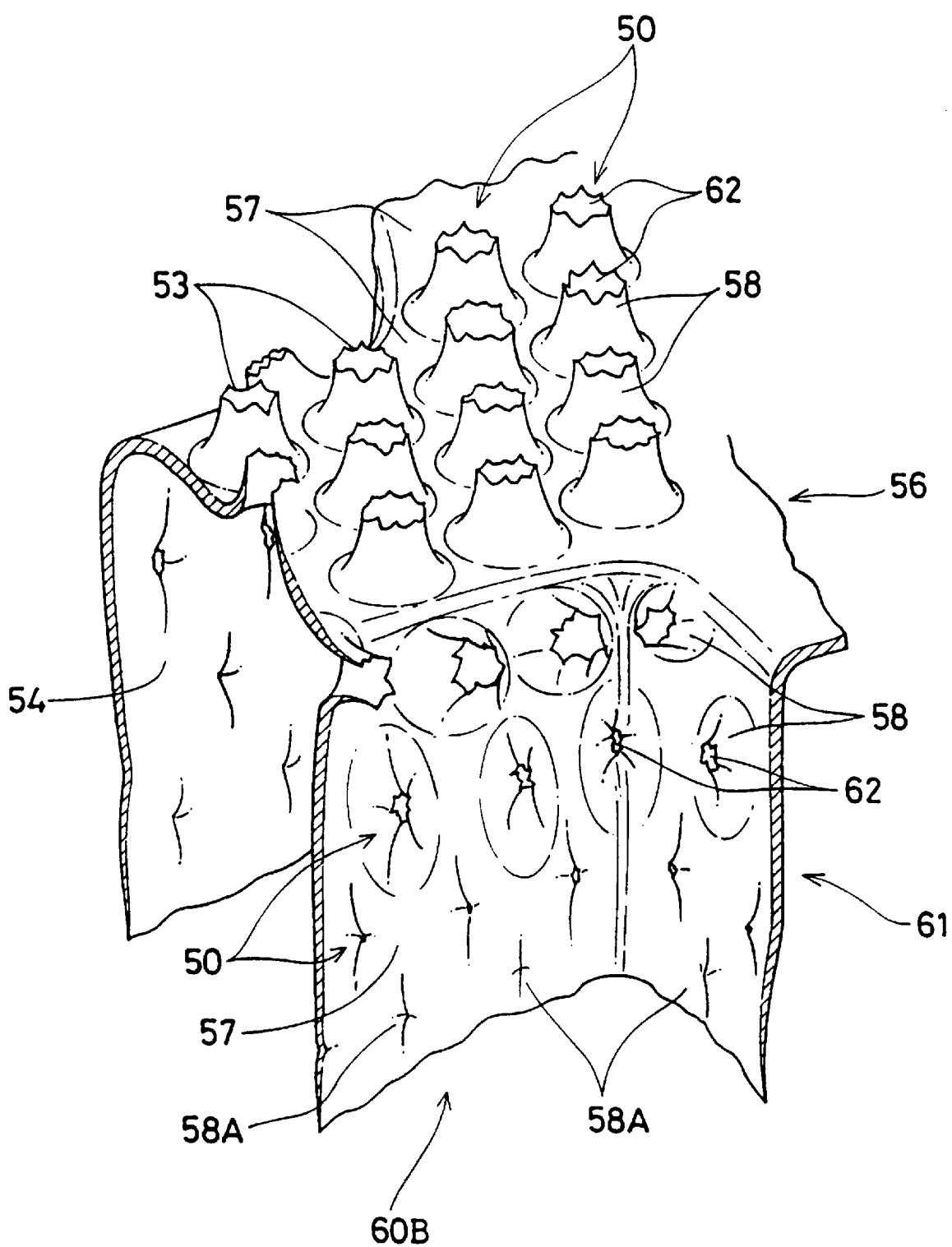
FIG. 13 is a greatly enlarged fragmentary perspective view of the plastic film after completion of the web forming process.

FIGS. 11–13 show the fully processed plastic film 10. The plastic film 10 shown in FIGS. 11–13 may be used for a body-facing material for an absorbent article. As will be apparent from the enlarged fragmentary perspective view of the plastic film 10 shown in FIG. 11, the fully processed plastic film 10 exhibits dimensionally stable, three-dimensional macro-apertures 60 and fine-scale, volcano-like micro-apertures 50. The plastic film 10 has a first surface 57 and a second surface 54. The plastic film 10 has a land area 56 which faces the wearer's body when the plastic film 10 is used as a topsheet of an absorbent article. The plastic film 10 also has volcano-like aberrations 58.

The land area 56 has a pattern of fine scale, volcano-like surface micro-apertures 50. The fine scale, volcano-like micro-apertures 50 comprise the volcano-like aberrations 58 and the micro-opening 62 at the top of the aberrations 58. The size of the micro-apertures 50 on the land area 56 may be defined by either of the average height of the aberrations 58 or the average area of the micro-openings 62 or by both of these. The micro-openings 62 on the land area 56 have an average aperture area which typically may be from 0.002 $mm^2$ and 0.2 $mm^2$. The aberrations 58 on the land area 56 protrude from the land area 56 beyond the first surface 57 of the land area 56. The aberrations 58 have an average height which typically may be from 0.05 mm and 0.5 mm. Each of the fine-scale, volcano-like micro-apertures 50 actually forms a small capillary network resembling a tiny volcano, the outermost edges of which end in silky and soft feeling cusps 53. Due to the tactile impression imparted to the plastic film 10 by cusps 53, the land area 56 of the plastic film 10 is normally perceived as well suited for sustained contact with the skin. As explained in the above process description, the fine-scale, volcano-like micro-apertures 50 are maintained on the first surface 57 generally without changing its shape.

The macro-apertures 60 are defined by the wall 61, an opening 60A located on the first surface 57 and the apex opening 60B. The size of the macro-apertures 60 is generally bigger than the size of the fine-scale, volcano-like micro-apertures 50 located on the land area 56. Preferably, the size of the macro-apertures 60 may be at least 4 times as big as the size of the micro-apertures 50. The wall 61 extends and protrudes beyond the second surface 54 of the land area 56. The wall 61 may have the fine-scale, volcano-like micro-apertures 50 on its surface. The fine-scale, volcano-like micro-apertures 50 on the wall 61 may also comprise the volcano-like aberrations 58 and the micro-opening 62 at the top of the aberrations 58. The size of the micro-apertures 50 on the wall 61 may be defined by either of the average height of the aberrations 58 or the average area of the micro-openings 62 or by both of these. The size of micro-apertures 50 on the wall 61 is generally smaller than that of the micro-apertures on the land area 56. As shown in FIGS. 12 and 13, both the height of the aberrations 58 and the aperture area of the micro-openings 62 are generally decreasing toward the apex opening 60B because the wall 61 of the plastic film 10 is heated and melted during the process as described above. While the micro-apertures 50 on the wall 61 shown in FIGS. 12 and 13 loses both the height and the area of the micro-apertures 50, they may maintain either of these. The micro-apertures 50 on the wall 61 may lose only its height of the aberrations 58. Alternatively, the micro-apertures 50 on the wall 61 may lose only its aperture area of the micro-openings 62. Consequently, the wall 61 becomes dimensionally stable and becomes stiffer than the land area 56 which has many micro-apertures 50 thereon. The wall 61 also becomes more resilient to be capable of withstanding and rebounding from a pressure which is given by the wearer when the plastic film 10 is used for an absorbent article topsheet. Further, losing the height of the volcano-like aberrations 58 and the area of the micro-openings 62, the wall 61 may have no micro-apertures at the region adjacent the apex opening 60B, or most or all region of the wall 61. Therefore, the number of the micro-apertures 50 per a unit area may be less on the wall 61 than the land area 56. In the embodiment shown in FIG. 13, although there is still aberrations adjacent the apex opening 60B, the aberrations 58A have lost the micro-opening on the top of the aberrations.

When the plastic film 10 is used for the absorbent article topsheet, the plastic film 10 shown in FIGS. 11–13 gives softer tactile impression to the wearer because the plastic film 10 has the fine-scale, volcano-like micro-apertures 50 with the cusps 53 on the land area 56. The plastic film 10 also shows good fluid acquisition because the macro-apertures 60 have a dimensionally stable shape of apertures which makes fluid penetrate easily. In addition, the plastic film 10 shows good rewet performance because the wall 61 of the macro-apertures has resiliency so that the wearer's skin is maintained at a distance away from an absorbent core which absorbs body fluid by interposing the resilient plastic film 10 therebetween.

Figure 14:
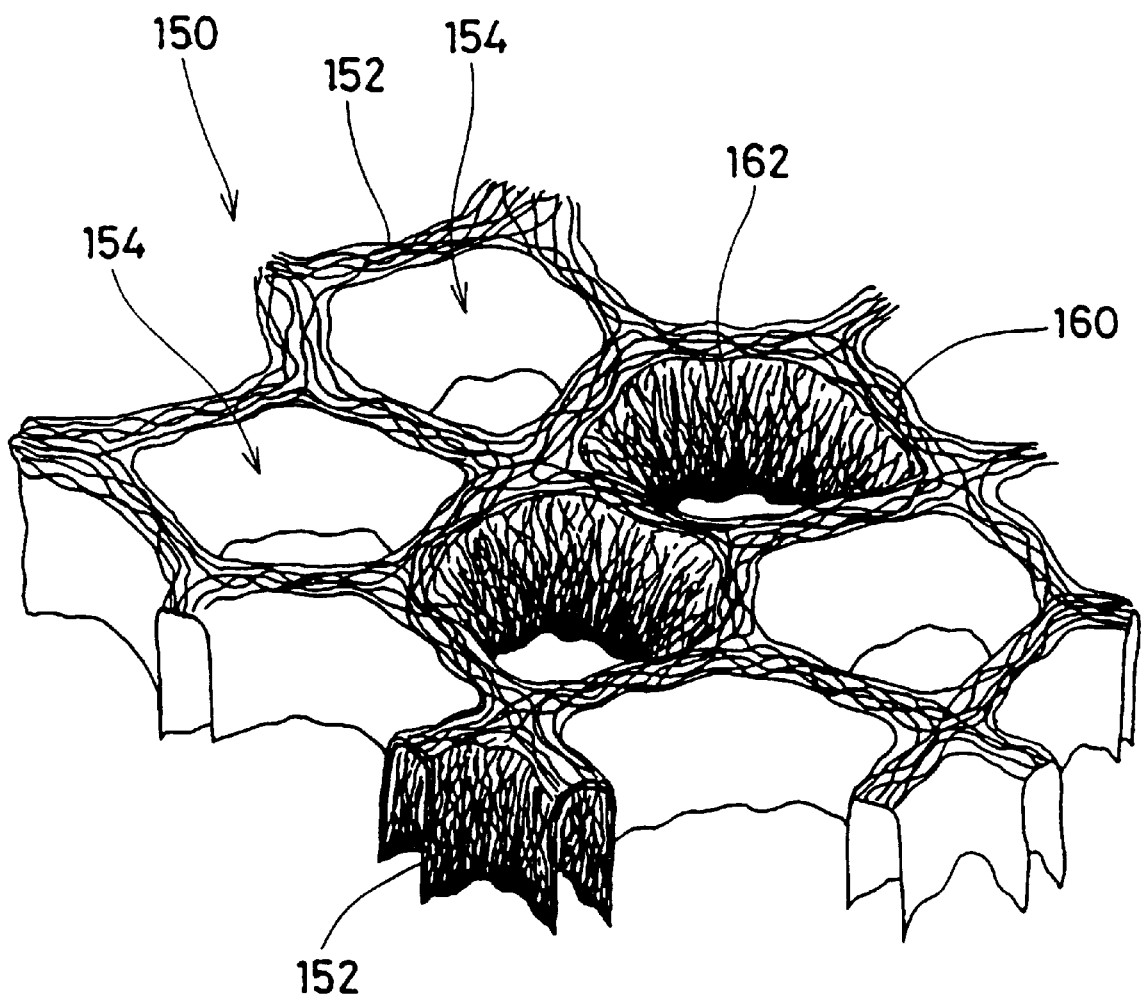
FIG. 14 is an enlarged fragmentary perspective view of a web comprising fiber aggregation after completion of the web forming process.
Figure 15:
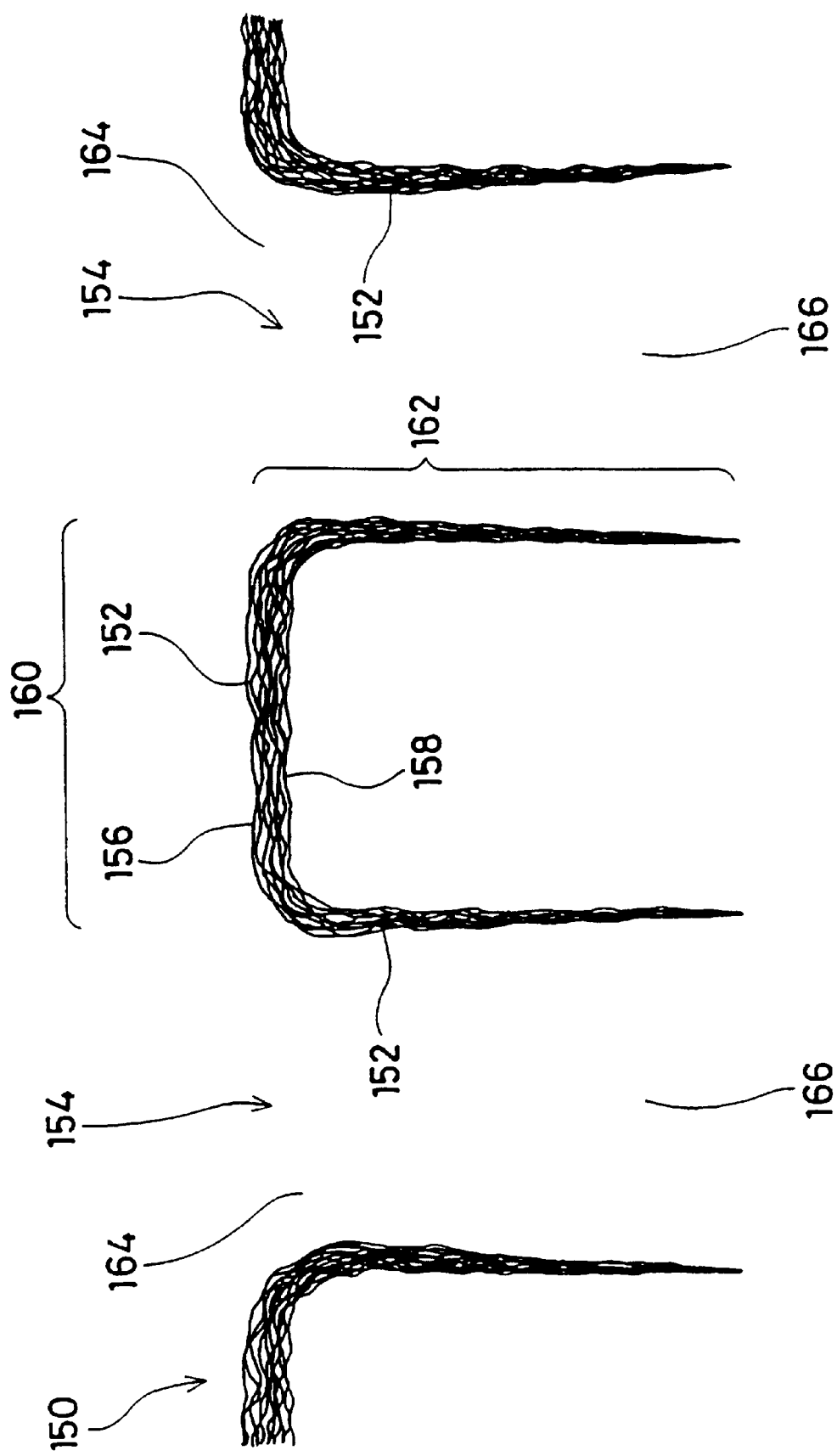
FIG. 15 is an enlarged cross-sectional view of the web comprising fiber aggregation after completion of the web forming process.

FIGS. 14–15 show alternative embodiment of the fully processed web 150 comprising fiber aggregation 152. The fibrous web 150 can be made from a fiber aggregation 152 which is formed as a nonwoven. The nonwoven may be processed only by the second process shown in FIG. 1 since the fibrous web 150 may not have micro-apertures on the land area. However, if desired, the nonwoven may be processed by both the first process and the second process shown in FIG. 1. Alternatively, a nonwoven may be processed by the process shown in FIG. 9 in order to get the processed fibrous web 150.

The fully processed fibrous web 150 exhibits dimensionally stable, three-dimensional macro-apertures 154. The fibrous web 150 may be used for a body-facing material for an absorbent article. The fibrous web 150 has a first surface 156 and a second surface 158. The fibrous web 150 has a land area 160 which upwardly faces the wearer's body when the fibrous web 150 is used as a topsheet of an absorbent article and a wall 162 which protrudes beyond the second surface 158 of the land area 160. The macro-apertures 154 are defined by the wall 162, an opening 164 on the first surface surrounded by the wall 162 and an apex opening 166.

The fibrous web 150 comprises fiber aggregation 152 which may include one fibrous layer or more layers. Each layer may comprise any type of thermoplastic fibers using such as polyethylene, polypropylene, polyester or any combination thereof. The thermoplastic fibers may be bi-component fibers using the above materials. The thermoplastic fibers may be of varying the cross-section. When the fiber aggregation 152 includes at least two layers having the first layer which is disposed adjacent the first surface 156 and the second layer which is disposed adjacent the second surface 158, each layer may comprise different types of thermoplastic fibers from each other. Further each layer may comprise different types of forming processes from each other, such as spunbond, carded or meltblown layers. Alternatively, they may comprise the same type of fibers. Optionally, the first layer disposed adjacent the first surface 156 may comprise less hydrophilic fibers than the second layer disposed adjacent the second surface 158 whereby the first layer becomes less hydrophilic than the second layer.

The land area 160 of the fibrous web 150 comprises fiber aggregation 152 and exhibits capillary network therein. The land area 160 of the fibrous web 150 gives soft tactile impression to the wearer and a soft feeling when the land area 160 touches the wearer's body.

A portion of the wall 162 also comprises the fiber aggregation 152. At least a portion of the fibers forming the wall 162 are melted and bonded to each other by, e.g., the above process whereby the fiber aggregation 152 on the wall 162 is densified at least at a portion. Preferably the fiber aggregation 152 may be melted and densified at least at a portion adjacent to the apex opening 166. Thereby the fiber aggregation 152 on the wall 162 may have a positive fiber density gradient from the opening 164 toward the apex opening 166 as schematically shown in FIGS. 14 and 15. Alternatively, most or all of the fiber aggregation 152 of the wall 162 may be melted and densified. The melted and densified fiber aggregation 152 becomes stiffer than the other portion of the fiber aggregation 152, such as the fiber aggregation 152 on the land area 160. The stiff wall also has more resiliency. Therefore, the wall 162 is capable of withstanding and/or rebounding from pressure given by the wearer when the fibrous web 150 is used as a topsheet of an absorbent article.

When the fibrous web 150 is used for the absorbent article topsheet, the fibrous web 150 shown in FIGS. 14 and 15 gives soft tactile impression to the wearer because the fibrous web 10 comprises the fiber aggregation 152 on the land area 160. The fibrous web 150 also shows good fluid acquisition because the macro-apertures 154 has a dimensionally stable shape of apertures which makes fluid penetrate easily. In addition, the fibrous web 150 shows good rewet performance because the wall 162 of the macro-apertures has resiliency so that the wearer's skin is maintained at a distance away from an absorbent core which absorbs body fluid by interposing the resilient fibrous web 150 therebetween.

Figure 16:
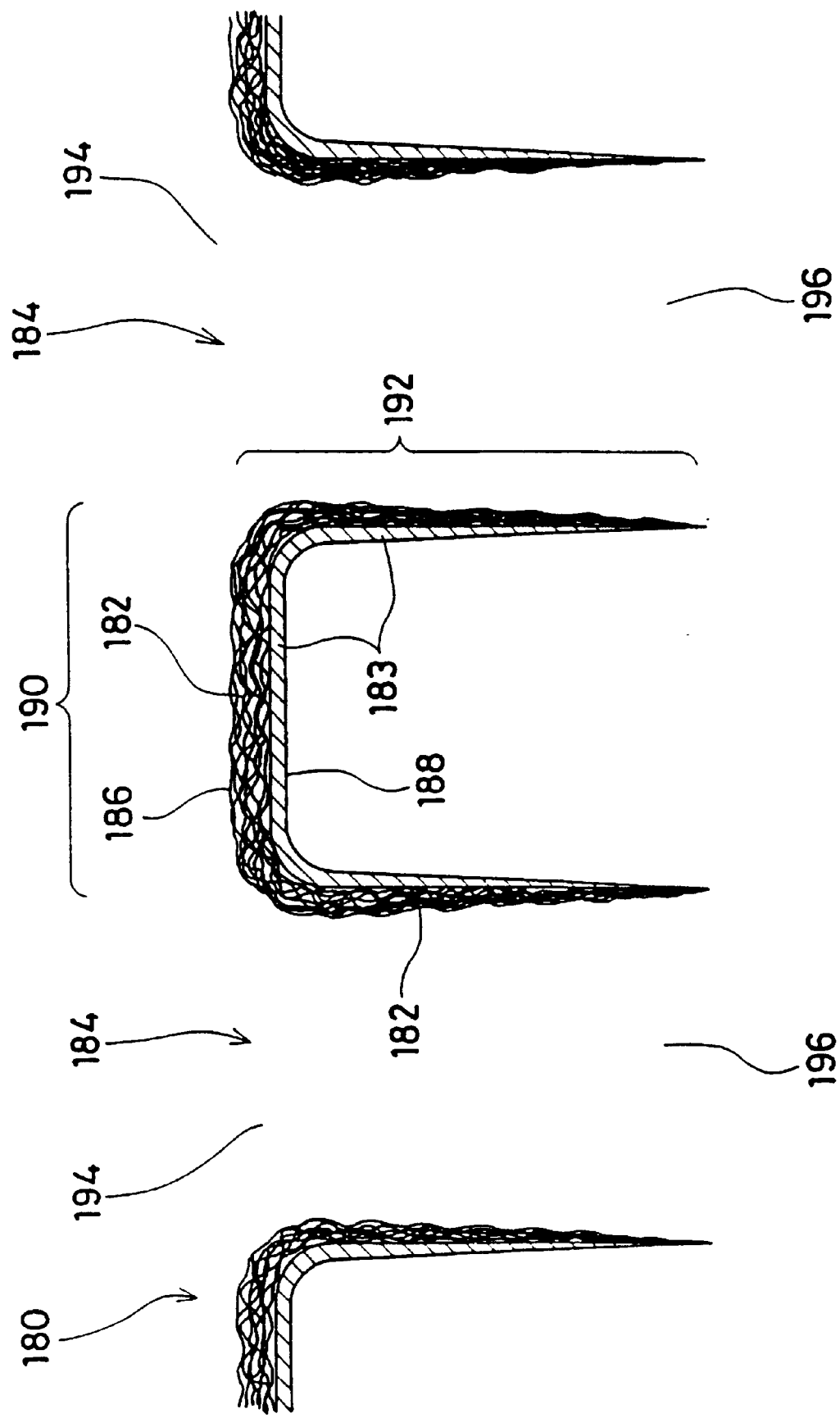
FIG. 16 is an enlarged cross-sectional view of a web comprising fiber aggregation and a plastic film after completion of the web forming process.

FIG. 16 shows a further alternative embodiment of the fully processed composite web 180 comprising fiber aggregation 182 and a plastic film 183. The composite web 180 can be made from a fiber aggregation 182 which is formed as a nonwoven and a plastic film 183. The nonwoven and the plastic film may be processed only by the second process shown in FIG. 1 since the composite web 180 may not have micro-apertures on the land area. However, if desired, a nonwoven and a plastic film which form the composite web 180 may be processed by both the first process and the second process shown in FIG. 1. Alternatively, a nonwoven and a plastic film may be processed by the process shown in FIG. 9 in order to get the composite web 180.

The fully processed composite web 180 exhibits dimensionally stable, three-dimensional macro-apertures 184. The composite web 180 may be used for a body-facing material for an absorbent article. The composite web 180 has a first surface-186 and a second surface 188. The composite web 180 has a land area 190 which upwardly faces the wearer's body when the composite web 180 is used as a topsheet of an absorbent article and a wall 192 which protrudes beyond the second surface 188 of the land area 190. The macro-apertures 184 are defined by the wall 192, an opening 194 on the first surface surrounded by the wall and an apex opening 196.

The composite web 180 may include fiber aggregation 182 which may have one fibrous layer or more layers. Each layer may comprise thermoplastic fibers which may be the same materials for the fiber aggregation 152 above. Further, the composite web 180 may include at least one thermoplastic film layer 183 which may comprise various materials, such as polyethylene, low density polyethylene, linear low density polyethylene, or polypropylene. Preferably, the materials for the fiber aggregation 182 and the thermoplastic film may comprise the chemically same or chemically similar type of materials such that the fiber aggregation 182 and the thermoplastic film 183 can be bonded when they are melted to each other. Preferably, the fiber aggregation 182 is disposed on the first surface 186 of the composite web 180 and the plastic film 183 is disposed on the second surface 188. The fiber aggregation 182 may be less hydrophilic than the plastic film 183 so that the composite web 180 has positive hydrophilicity gradient from the fiber aggregation 182 towards the plastic film 183.

The land area 190 of the composite web 180 comprises the fiber aggregation 182 and the plastic film 183, and exhibits capillary network therein. The fiber aggregation 182 on the first surface 186 of the land area 190 can be directly seen by the wearer, therefore gives soft tactile impression to wearer. The plastic film 183 on the second surface 188 of the land area 190 prevents body fluid, which is held in an absorbent core of an absorbent article, from leaking out toward the wearer's skin through the land area 190. Further, the plastic film 183 also serves to mask the color of the body fluid held in the absorbent core.

A portion of the wall 192 also comprises the fiber aggregation 182 and the plastic film 183. At least a portion of the fiber aggregation 182 on the wall 192 is melted and bonded to each other by, e.g., the above process whereby the fiber aggregation 182 on the wall 162 is densified at least at a portion. Preferably the fiber aggregation 182 may be melted and densified at least at a portion adjacent the apex opening 196. Thereby the fiber aggregation 182 on the wall 192 may have a positive fiber density gradient from the opening 194 toward the apex opening 196 as schematically shown in FIG. 16. Alternatively, most or all of the fiber aggregation 182 of the wall 192 may be melted and densified. Preferably, at least a portion of the fiber aggregation 182 on the wall 192 is melted and bonded to the plastic film 183. The plastic film 183 also may be melted and bonded with the fibers of the fiber aggregation 182. As schematically shown in FIG. 16, the fiber aggregation 182 and the plastic film 183 are melted to each other at least adjacent the apex opening 196. If desired, the fiber aggregation 182 and the plastic film 183 may be melted and bonded to each other on most or all portion of the wall 192. The melted and densified fiber aggregation 152 and the plastic film 183 which are bonded together become stiffer than the other portion of the fiber aggregation 152 and the plastic film 183, such as on the land area 190. The stiff wall also has more resiliency. Therefore, the wall 192 is capable of withstanding and/or rebounding from pressure given by the wearer when the fibrous web 180 is used as a topsheet of an absorbent article.

When the composite web 180 is used for the absorbent article topsheet, the composite web 180 shown in FIG. 16 gives a soft impression to the wearer because of the fiber aggregation 182 on the land area 190. The composite web 180 also shows good fluid acquisition because the macro-apertures 184 have a dimensionally stable shape of apertures which makes fluid penetrate easily. In addition, the composite web 180 shows good rewet performance because the wall 192 of the macro-apertures has resiliency so that the wearer's skin is maintained at a distance away from an absorbent core which absorbs body fluid by interposing the resilient composite web 180 therebetween. The composite web 180 also helps mask the color of body fluid which is held in the absorbent core.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A soft and resilient web exhibiting a substantially continuous three-dimensional pattern of macro-apertures, the web comprising a fluid impermeable plastic material, the web having a first surface, a second surface, a multiplicity of micro-apertures and a multiplicity of macro-apertures, wherein the web has a land area on the first surface and a wall protruding beyond the second surface of the land area, the land area includes a pattern of fine-scale, volcano-like micro-apertures comprising discrete volcano-like surface aberrations and micro-openings, the aberrations protruding from the land area beyond the first surface of the land area, and the micro-opening locating at the top of each aberration, the macro-apertures are defined by the wall, an opening on the first surface surrounded by the wall and an apex opening, and the wall has the micro-apertures thereon, the size of the micro-apertures on the wall is generally smaller than that of the micro-apertures on the land area.

2. The web of claim 1 wherein the number of the micro-apertures on the wall is less than the number of the micro-apertures on the land area, per a unit area.

3. The web of claim 1 wherein the size of micro-apertures on the wall decreases towards the apex opening of the macro-apertures.

4. The web of claim 1 wherein the wall is stiffer than the land area.

5. A soft and resilient web exhibiting a substantially continuous three-dimensional pattern of macro-apertures, the web comprising a fluid impermeable plastic material, the web having a first surface, a second surface, a multiplicity of micro-apertures and a multiplicity of macro-apertures, wherein the web has a land area on the first surface and a wall protruding beyond the second surface of the land area, the land area includes a pattern of fine-scale, volcano-like micro-apertures comprising discrete volcano-like surface aberrations and micro-openings, the aberrations protruding from the land area beyond the first surface of the land area, the micro-opening locating at the top of the aberration, the macro-apertures are defined by the wall, an opening on the first surface surrounded by the wall and an apex opening, and the wall has the micro-apertures thereon, the number of the micro-apertures on the wall is less than the number of the micro-apertures on the land area, per a unit area.

6. The web of claim 5 wherein the number of the micro-apertures on the wall decreases towards the apex opening of the macro-apertures, per a unit area.

* * * * *